United States Patent
De Angelis et al.

(10) Patent No.: US 12,208,388 B2
(45) Date of Patent: Jan. 28, 2025

(54) MICROFLUIDIC DEVICES AND METHODS FOR USING THE DEVICES

(71) Applicants: Fondazione Istituto Italiano di Tecnologia, Genoa (IT); Università Degli Studi Di Genova, Genoa (IT)

(72) Inventors: Francesco De Angelis, Genoa (IT); Andrea Barbaglia, Busto Arsizio (IT); Michele Dipalo, Genoa (IT); Francesco Tantussi, Pisa (IT)

(73) Assignees: Fondazione Istituto Italiano di Tecnologia, Genoa (IT); Università Degli Studi Di Genova, Genoa (IT)

( * ) Notice: Subject to any disclaimer, the term of this patent is extended or adjusted under 35 U.S.C. 154(b) by 947 days.

(21) Appl. No.: 17/277,608

(22) PCT Filed: Sep. 17, 2019

(86) PCT No.: PCT/IB2019/057799
§ 371 (c)(1),
(2) Date: Mar. 18, 2021

(87) PCT Pub. No.: WO2020/058833
PCT Pub. Date: Mar. 26, 2020

(65) Prior Publication Data
US 2022/0032296 A1    Feb. 3, 2022

(30) Foreign Application Priority Data

Sep. 19, 2018    (IT) .................. 102018000008717

(51) Int. Cl.
*B01L 3/00*      (2006.01)
*G01N 33/50*     (2006.01)

(52) U.S. Cl.
CPC .... *B01L 3/502715* (2013.01); *G01N 33/5005* (2013.01); *B01L 2300/0645* (2013.01); *B01L 2300/069* (2013.01)

(58) Field of Classification Search
CPC ....... B01L 3/502715; B01L 2300/0645; B01L 2300/069; B01L 3/502707;
(Continued)

(56) References Cited

U.S. PATENT DOCUMENTS

RE40,209 E     4/2008  Sugihara et al.
9,939,372 B2   4/2018  Cerignoli et al.
(Continued)

OTHER PUBLICATIONS

Zhang, Jiayi et al., "Optical detection of brain cell activity using plasmonic gold nanoparticles." Nano letters vol. 9,2 (2009): 519-24. (Year: 2009).*
(Continued)

*Primary Examiner* — P. Kathryn Wright
*Assistant Examiner* — Curtis A Thompson
(74) *Attorney, Agent, or Firm* — MH2 Technology Law Group LLP

(57) ABSTRACT

A microfluidic device may include: electrically conductive lower portions; electrically conductive first upper portions that are configured to receive an electrical signal; shielding portions opaque to an incident optical beam, wherein the shielding portions are between the lower portions and first upper portions, and wherein the shielding portions include through openings; and compartment(s) containing filler and markers dispersed in the filler. Each compartment may include lower chamber(s) and upper chamber(s) in fluid communication with each other via the through openings. Each lower chamber may extend between a respective through opening and the lower portions. Each upper chamber may extend between at least one respective through opening and the first upper portions. The markers may be (Continued)

configured to move between the upper chambers and the lower chambers in variable amounts, and may be configured to emit an optical emission beam when illuminated by the incident optical beam.

20 Claims, 4 Drawing Sheets

(58) Field of Classification Search
CPC ..... B01L 2300/0654; B01L 2300/0887; G01N 33/5005; G01N 33/526
See application file for complete search history.

(56) References Cited

U.S. PATENT DOCUMENTS

| | | | | |
|---|---|---|---|---|
| 2004/0043479 | A1* | 3/2004 | Briscoe | G01N 30/6095 |
| | | | | 435/288.5 |
| 2005/0179901 | A1* | 8/2005 | Ostlin | G01N 21/07 |
| | | | | 356/445 |
| 2005/0185569 | A1* | 8/2005 | Coombs | G01N 35/00069 |
| | | | | 369/275.3 |
| 2008/0025875 | A1* | 1/2008 | Martin | B01D 71/50 |
| | | | | 422/68.1 |
| 2017/0176338 | A1* | 6/2017 | Wu | G01N 21/6428 |
| 2023/0051647 | A1* | 2/2023 | De Angelis | G01N 33/48728 |
| 2023/0060283 | A1* | 3/2023 | De Angelis | G01N 33/5005 |

OTHER PUBLICATIONS

International Search Report and Written Opinion in corresponding International Application No. PCT/IB2019/057799 mailed on Dec. 6, 2019, 16 pages.

Ballini et al., "A 1024-Channel CMOS Microelectrode Array With 26,400 Electrodes for Recording and Stimulation of Electrogenic Cells in Vitro", IEEE Journal of Solid-State Circuits, vol. 49, No. 11, Nov. 2014, 15 pages.

Cerea et al., "Coaxial-like three-dimensional nanoelectrodes for biological applications", Microelectronic Engineering, vol. 187-188, Feb. 1, 2018, 6 pages.

Cerea et al., "Selective intracelluar delivery and intracellular recordings combined on MEA biosensors", Arxiv.org, Aug. 23, 2018, 20 pages.

Dipalo et al., "Plasmonic meta-electrodes allow intracellular recordings at network level on high-density CMOS-multi-electrode arrays", Nature Nanotechnology, Aug. 13, 2018, 12 pages.

Tantussi et al., "Long-Range Capture and Delivery of Water-Dispersed Nano-objects by Microbubbles Generated on 3D Plasmonic Surfaces", ACS Nano, vol. 12, No. 5, Mar. 28, 2018, 7 pages.

Tokuda et al., "Optical and Electric Multifunctional CMOS Image Sensors for On-Chip Biosensing Applications", Materials, vol. 4, No. 1, Dec. 29, 2010, 19 pages.

Zhang et al., "Optical Detection of Brain Cell Activity Using Plasmonic Gold Nanoparticles", Nano Letters, vol. 9, No. 2, Feb. 11, 2009, 6 pages.

* cited by examiner

MICROFLUIDIC DEVICES AND METHODS FOR USING THE DEVICES

CROSS-REFERENCE TO RELATED APPLICATION(S)

This application is a national stage entry from International Application No. PCT/IB2019/057799, filed on Sep. 17, 2019, in the Receiving Office ("RO/IB") of the International Bureau of the World Intellectual Property Organization ("WIPO"), and published as International Publication No. WO 2020/058833 A1 on Mar. 26, 2020; International Application No. PCT/IB2019/057799 claims priority from Italian Patent Application No. 102018000008717, filed on Sep. 19, 2018, in the Italian Patent and Trademark Office ("IPTO"), the entire contents of all of which are incorporated herein by reference.

TECHNICAL FIELD

The present invention relates to a microfluidic device and methods of using said device.

The microfluidic device of the present invention particular finds application in the measurement of the action potential of a cell in vitro.

BACKGROUND ART

The action potential is a signal of electrogenic cells, i.e. those cells that can modify the permeability of their membrane to certain ions in response to electrical or mechanical stimulation. The action potential is generated when the ion potential across the membrane exceeds a certain threshold, and it is transmitted to send information for muscle and hormone response regulation.

The electrical signal may be detected directly or indirectly. In the prior art, direct measurement requires a microelectrode array to detect cell excitation and/or acquire action potential, a signal amplifier and an instrument for displaying potentials.

Document US-RE 40209 discloses an exemplary direct-measurement device which is composed of a planar electrode having a microelectrode array on its surface for simultaneous detection of the action potentials generated by the cells on the electrode.

Concerning direct measurement of the action potential using arrays of planar electrodes, the document "Plasmonic meta-electrodes allow intracellular recordings at network level on high-density CMOS-multi-electrode arrays" (Nature Nanotechnology, 2018, Https://doi.org/10.1038/s41565-018-0222-z) represents the most recent and innovative implementation. In this document, the action potentials of thousands of electrogenic cells are measured with high sensitivity due to cell membrane poration by laser stimulation of plasmonic materials.

Indirect action potential measurement is carried out by conventional optical methods, using, for example, the devices as described in Zhang J. Atay, T., Nurmikko A. V., "Optical detection of brain cell activity using plasmonic gold nanoparticles", Nano Lett., 2009, 9 (2), pp 519-524 and U.S. Pat. No. 9,939,372 B2.

"Optical detection of brain cell activity using plasmonic gold nanoparticles", Zhang et al., 2009 describes optical measurement of surface plasmon resonance changed by the action potential of an electrogenic cell on a planar array of gold nanoparticles. This method can detect the electrical activity of cells using optical instruments only, without causing structural changes to the cell.

U.S. Pat. No. 9,939,372 B2 provides the introduction of fluorescent means into the cell, which responds to changes in membrane potential and ion concentration. If these means interact with an incident optical beam, they have distinct emission wavelengths. Each emitted wavelength is recorded by a photodetector and used in combination with the others for cytometric analysis.

Problem of the Prior Art

Although electrical signal direct detection is the most widespread techniques, due to high signal-to-noise ratio and simple acquisition, the introduction of electrodes may cause electrodes may cause structural damages to the cell. Furthermore, the achievable spatial resolution is lower as compared with that of an optical chamber.

The optical solution as described in "Optical detection of brain cell activity using plasmonic gold nanoparticles", Zhang et al., 2009 requires complex setups of cell simulation and signal acquisition. This is because, despite the important benefit of operating on unmodified cells, surface plasmon resonance requires a 850 nm laser emission incident on the array of gold nanoparticles.

The device disclosed in U.S. Pat. No. 9,939,372 B2, by Cerignoli et al. uses a totally optical approach, which is yet invasive. Action potential detection requires one or more potentially toxic fluorescent agents to be administered into the cell. Furthermore, the effects of the fluorescent agents are prone to degradation due to photobleaching.

SUMMARY OF THE INVENTION

The main object of the present invention is to provide a microfluidic device for measuring the electrical activity of cells that is non-invasive.

Another object of the present invention relates to cell activity assessment at any stage of cell growth, without changes in measurement sensitivity.

A further object of the present invention is to provide a device for measuring the electrical activity of a cell that has a simple and versatile structure.

Another object of the present invention is to provide entirely optical measurement, which affords a higher spatial resolution as compared to that provided by electrical measurement of the action potential.

These objects are fulfilled by the microfluidic device of claim 1.

An advantage of the device of the invention consists in the possibility of measuring cellular activity under physiological conditions, i.e. without the injection of the fluorescent agents or genetic modifications for generation of the light signal.

A further advantage of the device is that the cell is not affected by measurement.

Another advantage of the present invention is to provide a device for measuring the electrical activity of a cell that does not require external power supply, since the optical signal is directly activated by the action potential generated by the cell.

Finally, the spatial resolution of signal recording is higher than that obtained with direct detection of the electrical cell signal, due to the high density of optical sensors in the chamber.

BRIEF DESCRIPTION OF THE DRAWINGS

The characteristics and advantages of the present invention will result clear from the following detailed description of a possible practical embodiment, illustrated as a non-limiting example in the set of drawings, in which.

DETAILED DESCRIPTION

Figure 1:
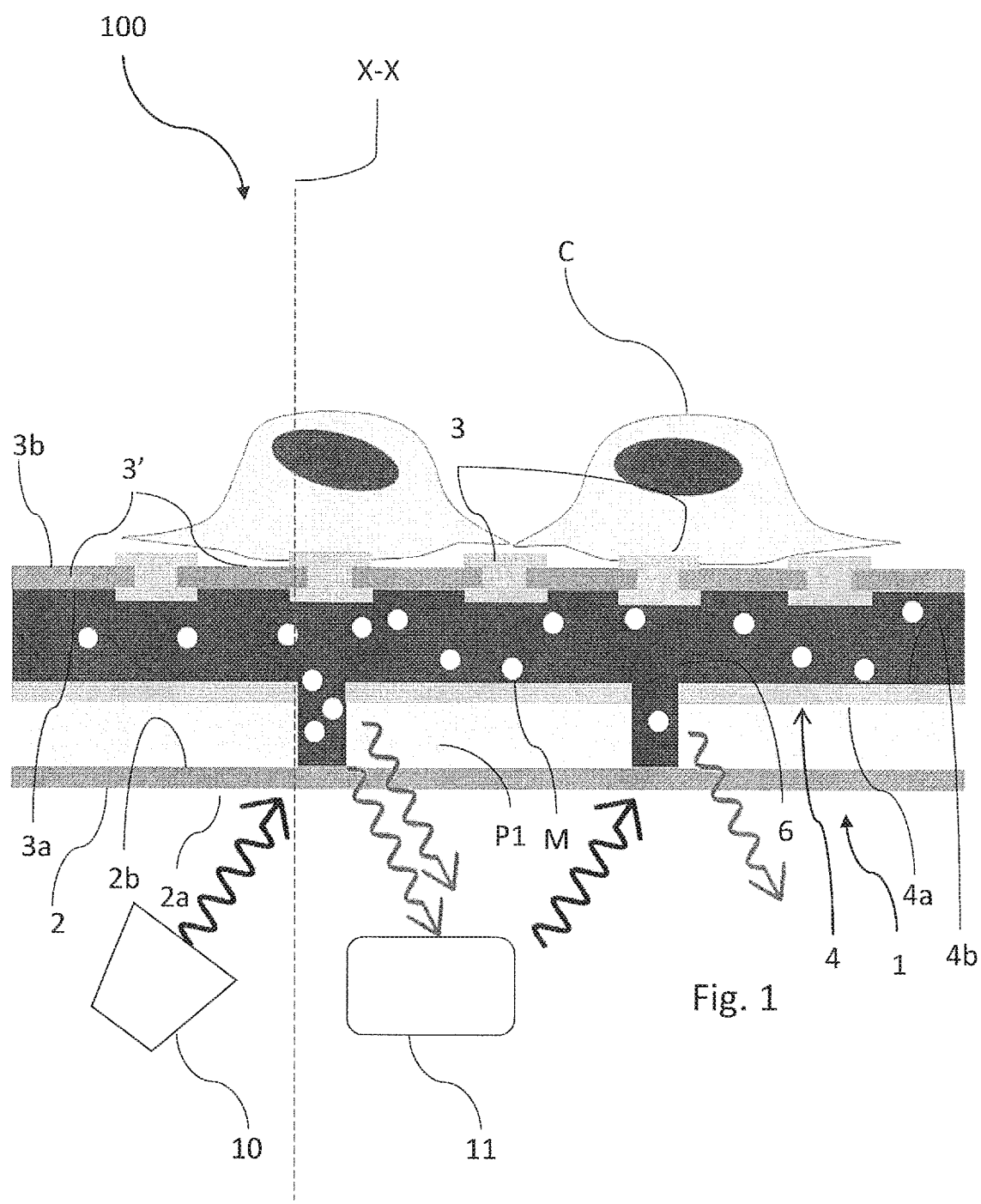
FIG. 1 shows a schematic view of an apparatus with a microfluidic device according to a first embodiment of the invention.

Referring to FIG. 1, there is shown a microfluidic device 1 according to the present invention.

The microfluidic device 1 comprises lower portions 2, first upper portions 3 and shielding portions 4 arranged between the first upper portions 3 and the lower portions 2.

The lower portions 2 are electrically conductive and are partly or totally transparent to an incident optical beam generated by an optical source 10.

The lower portions 2 identify a lower electrode and, in one embodiment, are defined by a lower layer of electrically conductive material, that is transparent to the incident optical beam.

This lower layer 2 has a bottom surface 2a and a top surface 2b, opposite to the bottom surface 2a.

The optical source 10 is configured to emit an incident optical beam toward the lower portions 2, in particular toward the bottom surface 2a of the lower layer 2.

The first upper portions 3 are electrically conductive and are configured to receive an electrical signal.

The first upper portions 3 identify an upper electrode and, in one embodiment, are defined by an upper layer of electrically conductive material.

This upper layer 3 has a bottom surface 3a and a top surface 3b, opposite to the bottom surface 3a.

In one embodiment, the first upper portions 3 comprise a plurality of upper electrodes, where each upper electrode is configured to receive a respective electric signal.

In a preferred embodiment, the electrically conductive first upper portions 3 are configured to accommodate at least one cell C and to receive an electrical signal of the action potential generated by the cell C. In this embodiment, the first upper portions 3 comprise a plurality of microelectrodes, each configured to accommodate a cell C or a portion of a cell C.

The first upper portions 3 are spaced apart from the lower portions 2 in a direction X-X transverse to the planes on which the lower portions 2 and the first upper portions 3 lie, i.e. extend.

According to a preferred embodiment, the microfluidic device 1 comprises second upper portions 3' disposed between contiguous first upper portions 3. Preferably, the second upper portions 3' are transparent to the optical emission beam. Preferably, the second upper portions 3' are electrically insulating. In other words, according to a preferred embodiment, the second upper portions 3' are transparent and the first upper portions 3 include electrodes that carry the electrical signal of the cells C on the top surface 3b to the bottom surface 3a of the first upper portions 3.

The shielding portions 4 are opaque to the incident optical beam and are arranged in the direction X-X between the first upper portions 3 and the lower portions 2. Preferably, the shielding portions 4 are made of a metal material, e.g. gold. In other words, the shielding portions 4 are opaque to the incident optical beam and are arranged between the first 3 and second 3' upper portions and the lower portions 2.

In one embodiment, the shielding portions 4 are defined by a shielding layer which is made of a material opaque to the incident optical beam.

These shielding portions 4 have a bottom surface 4a and a top surface 4b, opposite to the bottom surface 4a.

The shielding portions 4 are formed with through openings 5 which preferably extend in the direction X-X and whose function will be described hereinafter.

The device 1 comprises one or more compartments 6 containing a filler means 7 and markers M homogeneously dispersed in the filler means 7.

According to one embodiment, the markers M are selected between fluorophores having predetermined spectral emission, molecular weight and electric charge, quantum dots, nanorods and nanoparticles of predetermined size.

Preferably, the filler means 7 is a substance in a form of liquid or gel.

Each compartment 6 comprises at least one lower chamber 8 and at least one upper chamber 9 in fluid communication with each other via a respective through opening 5 formed in the shielding portions 4.

Each lower chamber 8 extends between the respective through opening 5 and the lower portions 2 and each upper chamber 9 extends between at least the through opening and the first upper portions 3.

The lower chambers 8 are separated by portions P1 of insulating material, which is optionally transparent to the incident optical beam, arranged between the lower portions 2 and the shielding portions 4. This insulating material, transparent to the incident optical beam may be, by way of example and without limitation, a polymeric material, or $Si_3N_4$ or $SiO_2$. In one embodiment, the lower chambers 8 are spaced apart from each other by a few tens of nm to a few tens of micrometers.

The markers M are electrically charged and are configured to move between an upper chamber 9 and one or more lower chambers 8 in variable amounts according to the intensity of the electric signal applied to the first upper portions 3 and to emit an optical emission beam at an emission wavelength when illuminated in the lower chamber 8 by the incident optical beam produced by the optical source 10. On the other hand, the markers M that remain in the upper chamber 9, will be shielded from the incident optical beam by the shielding portions 4.

The optical emission beam generated by the markers M in the lower chamber/s 8 is detected by an optical detection device 11, preferably a CCD or CMOS device, or an array of detectors and is filtered on the emission wavelength of the markers M to thereby generate an optical signal representative of the electric signal applied to the first upper portions 3.

According to a preferred arrangement, the markers M are configured to emit the optical emission beam through the lower portions 2.

According to a preferred arrangement, which may be provided instead of or in combination with the previous arrangement, the markers M are configured to emit the optical emission beam through the second upper portions 3' which, as set forth above, are transparent to the optical emission beam.

The microfluidic device 1 with the optical source 10 and the optical detection device 11 form an apparatus referenced 100 in the accompanying figures.

According to a preferred embodiment, each compartment 6 comprises a plurality of lower chambers 8 shaped as a plurality of lower cavities extending between one respective through opening 5 and the lower portions 2 to form an array of lower cavities.

As mentioned above, these lower cavities 8 are separated by portions of insulating material P1, which is optionally transparent to the incident optical beam, arranged between the lower portions 2 and the shielding portions 4.

In the embodiment of FIG. 1, the upper chamber 9 continuously extends between the first upper portions 3 and the shielding portions 4 with their respective through openings and is in fluid communication with the lower cavities 8 via these through openings 5.

Figure 2:
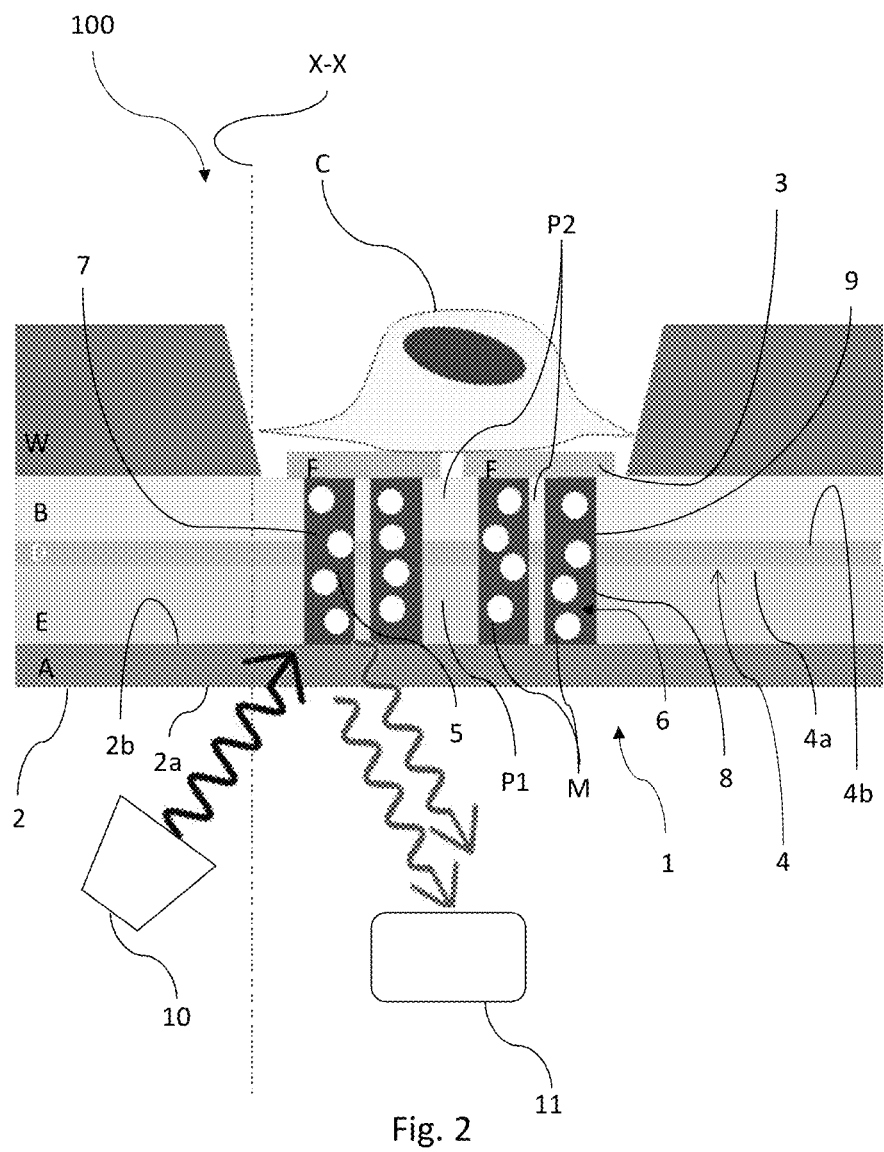
FIG. 2 shows a schematic view of an apparatus with a microfluidic device according to a second embodiment of the invention.

In the embodiment of FIG. 2, each compartment 6 comprises a plurality of upper chambers 9 shaped as a plurality of upper cavities extending between the respective through opening 5 and the first upper portions 3 to form an array of upper cavities, where each upper cavity 9 is in fluid communication with a respective lower cavity 8. In this embodiment, these upper cavities 9 are separated by portions P2 of insulating material, arranged between the first upper portions 3 and the shielding portions 4. Like in the portions P1 of insulating material that separate the lower cavities 8, this insulating material may be, by way of example and without limitation, a polymeric material or $Si_3N_4$ or $SiO_2$.

In the presence of a liquid, the markers M can move from an upper chamber 9 toward one or more lower chambers 8 and vice versa from these lower chambers 8 toward the upper chamber 9, according to the intensity and the sign of the electric potential applied to the first upper portions 3 and the amount and the sign of the electrical charge, the molecular weight, and the concentration of the markers M.

Thus, when an electrical signal is applied to the first upper portions 3 in the form of a pulse, the markers M can move from the upper chambers 9 toward the lower chambers 8 during the rising edge of the electrical signal and from the lower chambers 8 toward the upper chambers 9 during the falling edge of the electrical signal or vice versa, according to the electric charge of the markers M. In this configuration, the optical emission beam generated by the markers M in the lower chamber/s 8 and filtered and detected by the optical detection device 11 can generate an optical signal representative of the shape of the pulse of the electrical signal applied to the first upper portions 3.

On the other hand, in the presence of a gel, the markers M can move from an upper chamber 9 toward one or more lower chambers 8 and maintain the position in the lower chambers 8 when there is no electrical signal, while still being able to move from the lower chambers 8 to the upper chamber 9 when there is an electrical signal of sufficient intensity and of opposite sign.

This arrangement is particularly advantageous to form optically readable non-volatile memories with very low activation voltages, of the order of a few mV. This is because in the presence of a gel the markers M remain in a fixed position in the lower chamber 8 and the optical emission beam generated thereby remains constant due to their position and may be read several times, by means of the optical detection device 11. It shall be noted that the microfluidic device of the present invention may be used in the formation of a neuromorphic chip.

In this configuration, each lower chamber 8 may represent a bit whose value may be changed or written with a few mV applied to the first upper portions 3 and read, in the optical mode, by means of the optical detection device 11. It shall be noted that, in the memory application, the potential may also be external and hence not necessarily generated from a biological element, such as the cell C.

According to one embodiment, the microfluidic device 1 as schematically shown in FIG. 2 has a structural configuration with two initially separated parts, that are assembled into a multilayer during the manufacturing process as described below.

The first part, i.e. the lower portions 2, comprise a substrate A, preferably made of glass, which is coated at its top with a transparent conductive coating, preferably made of indium-tin oxide, ITO, i.e., indium oxide doped with tin.

The second part comprises the first upper portions 3 and the shielding portions 4. The first upper portions 3 comprise a membrane B, preferably made of silicon nitride $Si_3N_4$, formed on a silicon wafer W. The shielding portions 4 are formed by depositing on the $Si_3N_4$ membrane B an opaque optical layer, preferably made of metal.

Then, an additional optionally transparent insulating layer E, preferably made of $Si_3N_4$ or silicon oxide $SiO_2$, is deposited on the opaque optical layer D. Once the matrix of the multilayer E, D, B, W is completed, arrays of lower cavities 8 and upper cavities 9 are formed as through openings 5, and thereby opening nanocavities between the two sides of the multilayer E, D, B.

The upper openings of nanocavities at the membrane B are closed by forming one or more gold electrodes F with the cells C being able to be cultivated thereon. The gold electrodes F form the first upper portions 3.

The gold electrodes F lie over the array of upper cavities and act as plugs, i.e. block the upper openings of the through openings. For the final assembly of the microfluidic device 1, a drop of fluid filler 7 with fluorophores or other markers M is deposited on the ITO-coated glass substrate.

Then, the second part comprising the assembly of the first upper portions 3 and of the shielding portions 4 is placed on and is joined to the first part consisting of the substrate A, to thereby combine together the two parts of the multilayer and form the microfluidic device 1 as shown in FIG. 2. By this arrangement, the fluid with fluorophores is trapped between the ITO-coated glass substrate A and the multilayer E, D, B, W, F, thereby filling the arrays of lower cavities 8 and upper cavities 9.

Figure 3:
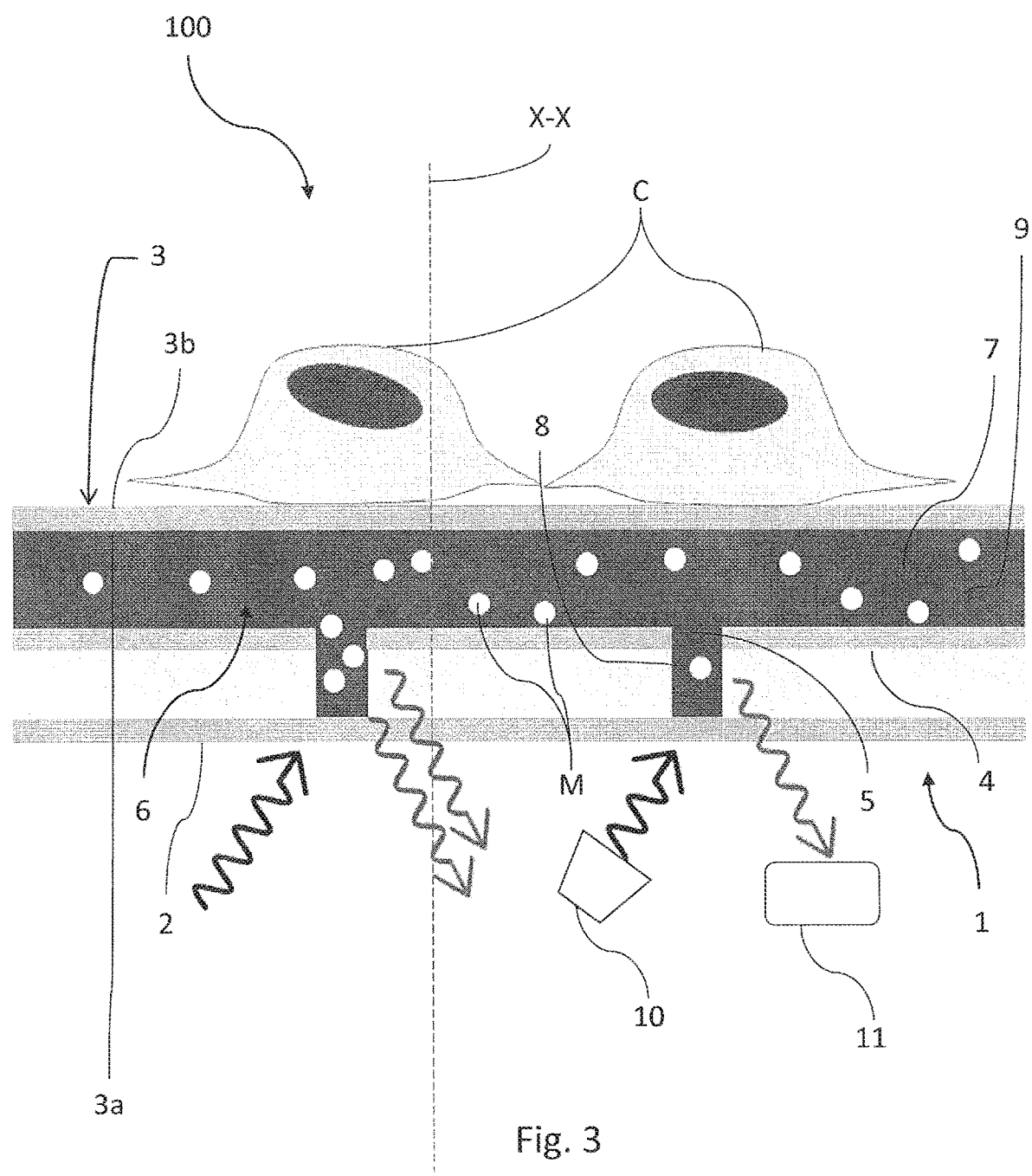
FIG. 3 shows a schematic view of an apparatus with a microfluidic device according to a third embodiment of the invention.
Figure 4:
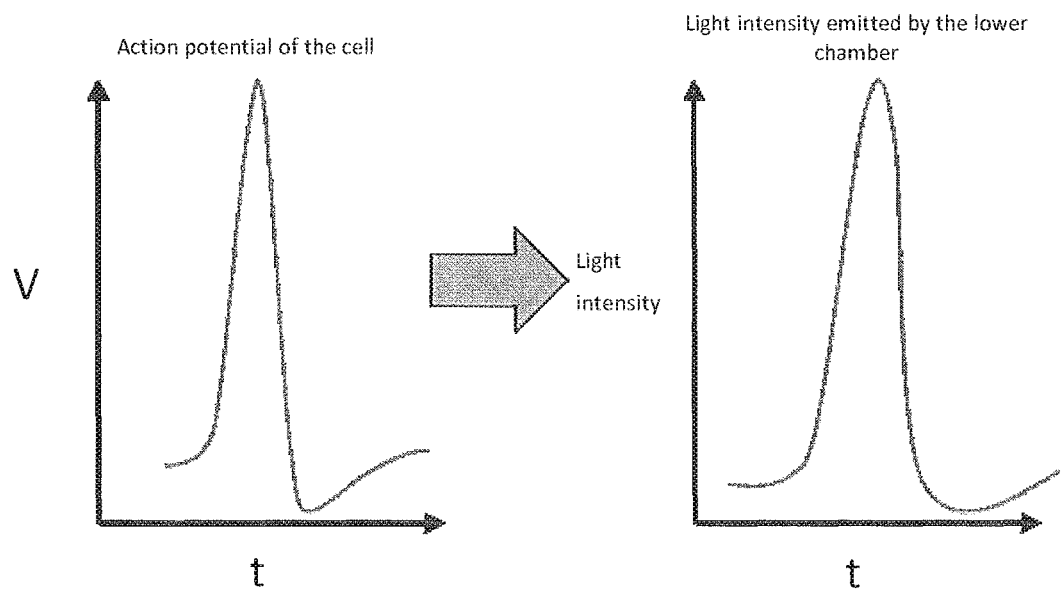
FIG. 4 shows the curves of an electric signal applied to the microfluidic device of FIGS. 1 to 3 and of an optical emission signal emitted by the device.
Figure 5:
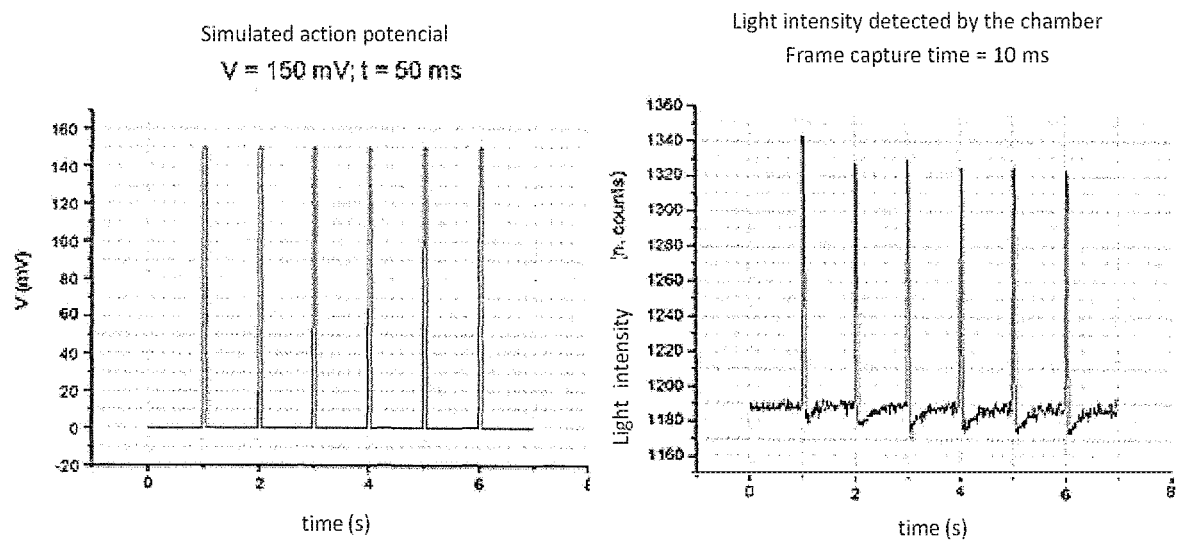
FIG. 5 shows electrical and optical signal curves obtained through experimental tests using the apparatus of FIG. 1.

The microfluidic device 1 as shown in FIGS. 1 and 3 is manufactured using a method that is similar to the method as used for the manufacture of the embodiment of FIG. 2, with minor changes. For example, the array of lower cavities 8 is obtained by forming a series of through openings 5 in the shielding portions 4 and in the underlying portions P1 of insulating material of the multilayer, while the volume of the upper chamber 9 continuously extending between the first upper portions 3 and the shielding portions 4 is left clear.

The invention claimed is:
1. A microfluidic device, comprising:
lower portions electrically conductive and transparent to an incident optical beam;
first upper portions electrically conductive and configured to receive an electrical signal;
shielding portions opaque to the incident optical beam and arranged between the first upper portions and the lower portions, the shielding portions having one or more through openings; and
one or more compartments containing filler means and markers dispersed in the filler means;

wherein each of the one or more compartments comprises one or more lower chambers and one or more upper chambers in fluid communication with each other via the one or more through openings,
wherein each of the one or more lower chambers extends between a respective through opening and the lower portions,
wherein each of the one or more upper chambers extends between at least one respective through opening and the first upper portions, and
wherein the markers are electrically charged and are configured to move between one of the one or more upper chambers and one of the one or more lower chambers in variable amounts according to an intensity of the electrical signal applied to a respective first upper portion, and are configured to emit an optical emission beam when illuminated in a respective one of the one or more lower chambers by the incident optical beam.

2. The microfluidic device of claim 1, wherein the markers are configured to emit the optical emission beam through the lower portions.

3. The microfluidic device of claim 1, further comprising:
second upper portions arranged between contiguous first upper portions;
wherein the second upper portions are transparent to the optical emission beam.

4. The microfluidic device of claim 3, wherein the markers are configured to emit the optical emission beam through the second upper portions.

5. The microfluidic device of claim 3, wherein the second upper portions are electrically insulating.

6. The microfluidic device of claim 1, further comprising:
a plurality of the one or more lower chambers shaped as a plurality of lower cavities extending between a respective through opening of the one or more through openings and the lower portions to form an array of lower cavities.

7. The microfluidic device of claim 6, further comprising:
a plurality of the one or more upper chambers shaped as a plurality of upper cavities extending between a respective through opening of the one or more through openings and the first upper portions to form an array of upper cavities;
wherein each upper cavity in the array of upper cavities is in fluid communication with a respective lower cavity in the array of lower cavities.

8. The microfluidic device of claim 6, wherein the one or more upper chambers of a respective compartment of the one or more compartments continuously extends between the shielding portions and the first upper portions so as to be in fluid communication with the plurality of lower cavities via the one or more through openings.

9. The microfluidic device of claim 1, wherein the filler means is in a form of liquid or gel.

10. The microfluidic device of claim 1, wherein the markers are selected from among:
fluorophores having predetermined spectral emission, molecular weight, and electrical charge;
quantum dots;
nanorods; and
nanoparticles of predetermined size.

11. The microfluidic device of claim 1, wherein the first upper portions comprise a plurality of upper electrodes, and
wherein each of the upper electrodes is configured to receive a respective electrical signal.

12. The microfluidic device of claim 1, wherein the first upper portions are configured to accommodate one or more cells and to receive the electrical signal corresponding to an action potential generated by an excited cell of the one or more cells.

13. An apparatus, comprising:
the microfluidic device of claim 1;
an optical source configured to emit the incident optical beam and to direct the incident optical beam toward the lower portions of the microfluidic device; and
an optical detection device configured to receive the optical emission beam emitted by the markers.

14. A method of measuring action potential of a cell using the apparatus of claim 13, the method comprising:
providing the cell on a respective first upper portion of the first upper portions;
generating the incident optical beam using the optical source; and
receiving the optical emission beam and filtering a predetermined wavelength of the optical emission beam.

15. A method of storing data using the microfluidic device of claim 11, the method comprising:
receiving a plurality of electrical signals using the plurality of upper electrodes;
generating the incident optical beam using an optical source; and
receiving the optical emission beam and filtering a predetermined wavelength of the optical emission beam.

16. A microfluidic device, comprising:
lower portions that are electrically conductive;
first upper portions that are electrically conductive and configured to receive an electrical signal;
shielding portions opaque to an incident optical beam, wherein the shielding portions are between the lower portions and the first upper portions, and wherein the shielding portions comprise one or more through openings; and
one or more compartments containing filler and markers dispersed in the filler;
wherein each of the one or more compartments comprises one or more lower chambers and one or more upper chambers in fluid communication with each other via the one or more through openings,
wherein each of the one or more lower chambers extends between a respective through opening and the lower portions,
wherein each of the one or more upper chambers extends between at least one respective through opening and the first upper portions, and
wherein the markers are electrically charged and are configured to move between one of the one or more upper chambers and one of the one or more lower chambers in variable amounts, and are configured to emit an optical emission beam when illuminated in a respective one of the one or more lower chambers by the incident optical beam.

17. The microfluidic device of claim 16, wherein the lower portions are totally transparent to the incident optical beam.

18. The microfluidic device of claim 16, wherein the lower portions are partly transparent to the incident optical beam.

19. The microfluidic device of claim 16, wherein the markers are configured to move between the one of the one or more upper chambers and the one of the one or more lower chambers in the variable amounts according to an intensity of the electrical signal applied to the respective first upper portion.

20. The microfluidic device of claim 16, wherein the markers are configured to move between the one of the one or more upper chambers and the one of the one or more lower chambers in the variable amounts according to a sign of the electrical signal applied to the respective first upper portion.

\* \* \* \* \*